United States Patent [19]

Chen et al.

[11] Patent Number: 5,541,104
[45] Date of Patent: Jul. 30, 1996

[54] MONOCLONAL ANTIBODIES WHICH BIND TO TUMOR REJECTION ANTIGEN PRECURSOR MAGE-1

[75] Inventors: Yao-Tseng Chen; Elisabeth Stockert; Yachi Chen, all of New York, N.Y.; Pilar Garin-Chesa; Wolfgang J. Rettig, both of Biberach, Germany; Pierre van der Bruggen; Thierry Boon-Falleur, both of Brussels, Belgium; Lloyd J. Old, New York, N.Y.

[73] Assignees: Ludwig Institute for Cancer Research, New York; Cornell Research Foundation, Inc., Ithaca, both of N.Y.

[21] Appl. No.: 190,411

[22] Filed: Feb. 1, 1994

Related U.S. Application Data

[63] Continuation-in-part of Ser. No. 37,230, filed as PCT/US92/04354, May 22, 1992, which is a continuation-in-part of Ser. No. 807,043, Dec. 12, 1991, Pat. No. 5,342,774, which is a continuation-in-part of Ser. No. 764,365, Sep. 23, 1991, abandoned, which is a continuation-in-part of Ser. No. 728,838, Jul. 9, 1991, abandoned, which is a continuation-in-part of Ser. No. 705,702, May 23, 1991, abandoned.

[51] Int. Cl.[6] .............. C12P 21/04; C12P 21/08; C12N 5/00; C07K 16/00

[52] U.S. Cl. .................. 435/240.27; 435/69.6; 435/70.21; 435/172.2; 530/350; 530/387.7; 530/388.8; 935/15; 424/138.1; 424/155.1; 424/174.1

[58] Field of Search .................. 435/69.1, 69.6, 435/69.3, 70.21, 91, 172.2, 172.3, 320.1, 235.1, 255, 256, 240.2, 240.27, 253.3, 388.8; 536/23.5; 530/350, 387.7; 935/9, 32, 34, 57, 62, 70, 71; 424/138.1, 155.1, 174.1

[56] References Cited

U.S. PATENT DOCUMENTS 5,342,774  8/1994  Boon et al. ..................... 435/240.2

FOREIGN PATENT DOCUMENTS

WO9220356  6/1992  WIPO.

*Primary Examiner*—Robert C. Budens
*Assistant Examiner*—T. Michael Nisbet
*Attorney, Agent, or Firm*—Felfe & Lynch

[57] ABSTRACT

The invention relates to monoclonal antibodies which specifically bind to the tumor rejection antigen precursor molecule MAGE-1, hybridomas which produce these monoclonal antibodies, and their use. Also described is a recombinant form of MAGE-1, peptides which are useful as immunogens, and immunogenic compositions containing the peptides and an adjuvant.

4 Claims, 5 Drawing Sheets

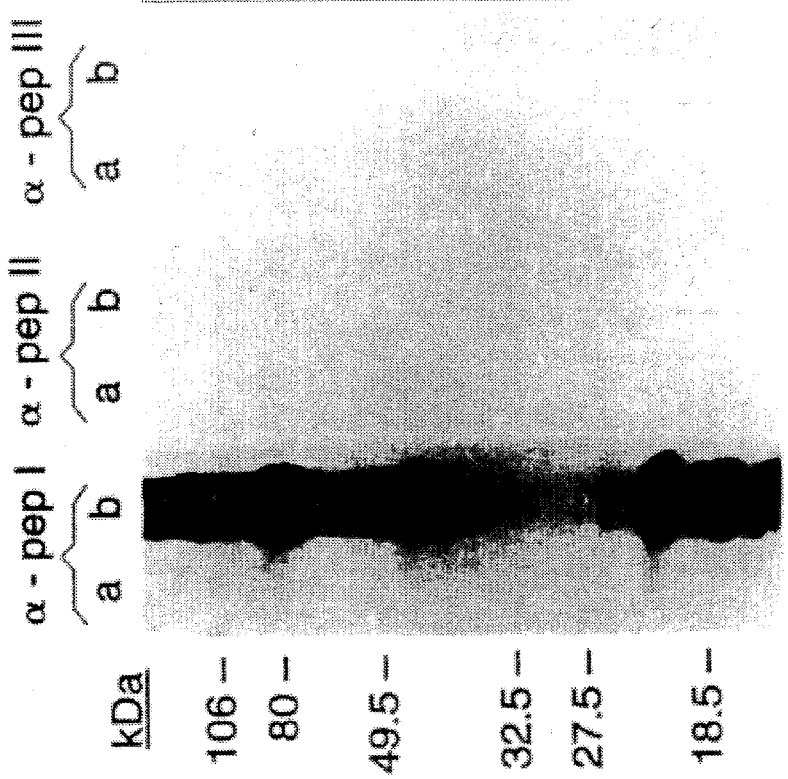
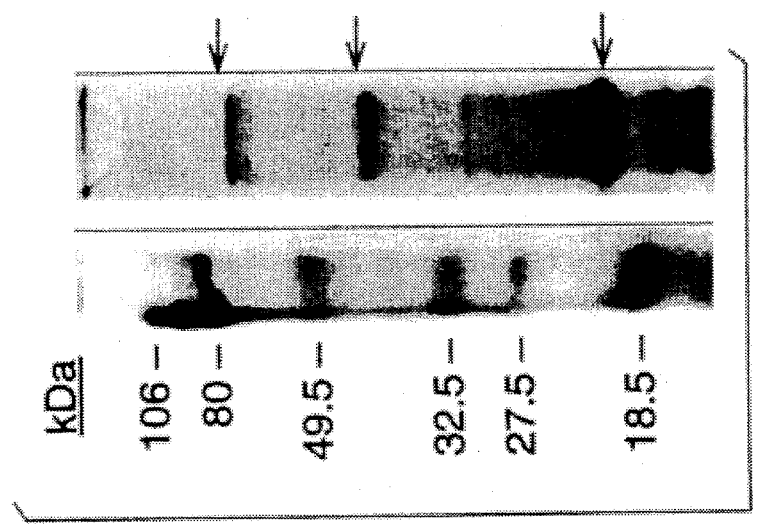

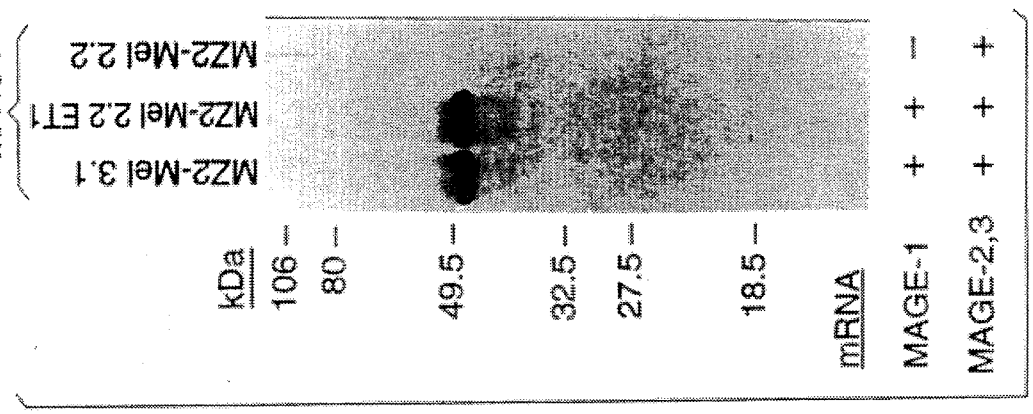
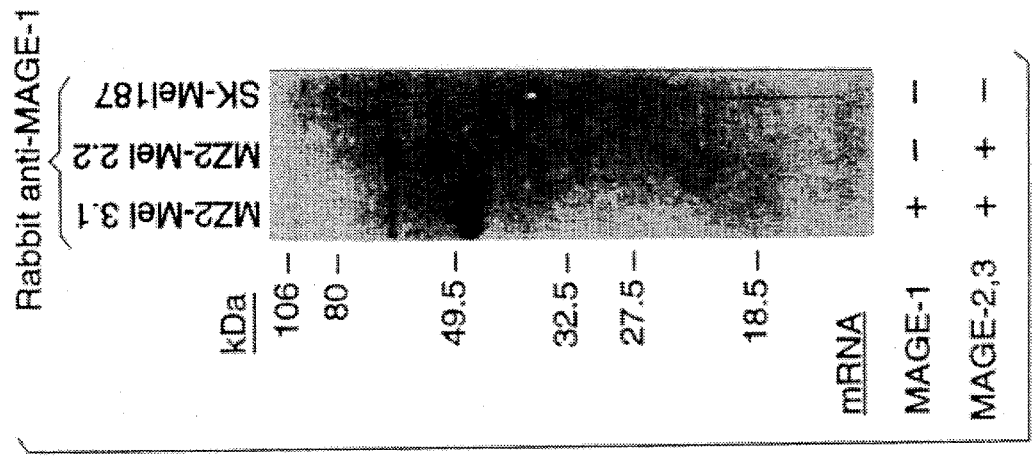
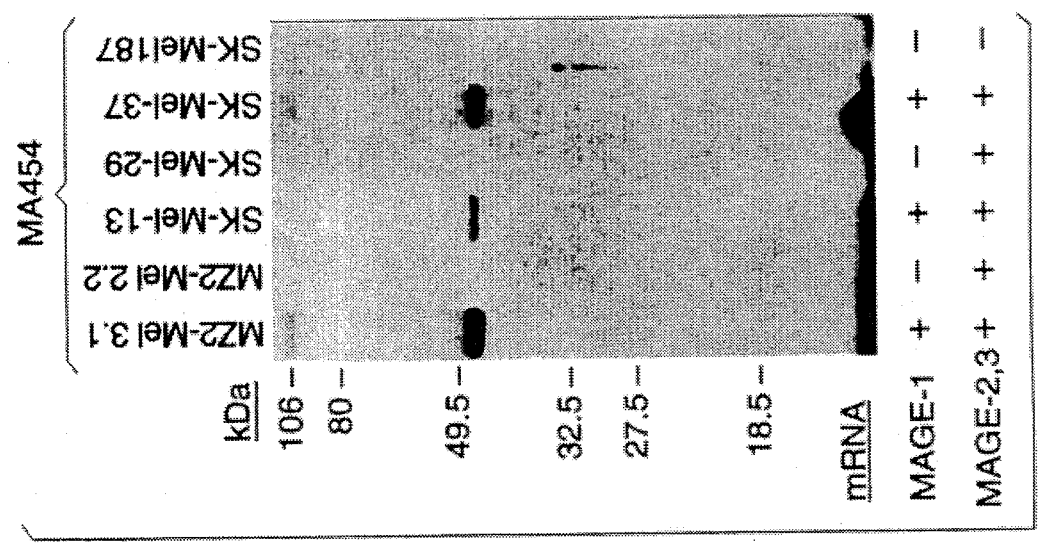

MONOCLONAL ANTIBODIES WHICH BIND TO TUMOR REJECTION ANTIGEN PRECURSOR MAGE-1

RELATED APPLICATION

This application is a continuation-in-part of Ser. No. 037,230 filed Mar. 26, 1993, which is itself a continuation-in-part of PCT Application PCT/US92/04354 filed on May 22, 1992 designating the United States, which is a continuation-in-part of Ser. No. 807,043, filed Dec. 12, 1991, now U.S. Pat. No. 5,342,774, which is a continuation-in-part of Ser. No. 764,365, filed Sep. 23, 1991, now abandoned, which is a continuation-in-part of Ser. No. 728,838, filed Jul. 9, 1991, now abandoned, which is a continuation-in-part of Ser. No. 705,702, filed May 23, 1991, and now abandoned.

FIELD OF THE INVENTION

This invention relates in general to the field of immunogenetics as applied to the study of oncology. More specifically, it relates to the study and analysis of mechanisms by which tumors are recognized by the organism's immune system such as through the presentation of so-called tumor rejection antigens, and the expression of what will be referred to herein as "tumor rejection antigen precursors" or "TRAPs". Most specifically, it refers to one such TRAP, i.e., MAGE-1, produced recombinantly, and monoclonal antibodies and antisera directed against MAGE-1, as well as their use.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum⁻ variants fail to form progressive tumors because they elicit an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl, Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearson et al., Cancer Res. 48: 2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including major histocompatibility antigens, the male specific H-Y antigens, and a class of antigens, referred to as "tum⁻" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45(1990), the disclosures of which are incorporated by reference. The P815 tumor is a mastocytoma, induced in a DBA/2 mouse with methylcholanthrene and cultured as both an in vitro tumor and a cell line. The P815 line has generated many tum$^-$ variants following mutagenesis, including variants referred to as P91A (DePlaen, supra), 35B (Szikora, supra), and P198 (Sibille, supra). In contrast to tumor rejection antigens—and this is a key distinction—the tum$^-$ antigens are only present after the tumor cells are mutagenized. Tumor rejection antigens are present on cells of a given tumor without mutagenesis. Hence, with reference to the literature, a cell line can be tum$^+$, such as the line referred to as "P1", and can be provoked to produce tum$^-$ variants. Since the tum$^-$ phenotype differs from that of the parent cell line, one expects a difference in the DNA of tum$^-$ cell lines as compared to their tum$^+$ parental lines, and this difference can be exploited to locate the gene of interest in tum$^-$ cells. As a result, it was found that genes of tum$^-$ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum$^-$ antigen are presented by the L$^d$ molecule for recognition by CTLs. P91A is presented by L$^d$, P35 by D$^d$ and P198 by K$^d$.

Prior patent applications PCT/US92/04354, U.S. Ser. Nos. 807,043, now U.S. Pat No. 5,342,774; 764,364, now abandoned; 728,838, now abandoned, and 707,702, now abandoned, all of which are incorporated by reference, describe inventions involving, inter alia, genes and other nucleic acid molecules which code for various TRAPs, which are in turn processed to tumor rejection antigen, or "TRAs".

The genes are useful as a source for the isolated and purified tumor rejection antigen precursor and the TRA themselves, either of which can be used as an agent for treating the cancer for which the antigen is a "marker", as well as in various diagnostic and surveillance approaches to oncology, discussed infra. It is known, for example, that tum$^-$ cells can be used to generate CTLs which lyse cells presenting different tum$^-$ antigens as well as tum$^+$ cells. See, e.g., Maryanski et al., Eur. J. Immunol 12: 401 (1982); and Van den Eynde et al., Modern Trends in Leukemia IX (June 1990), the disclosures of which are incorporated by reference. The tumor rejection antigen precursor may be expressed in cells transfected by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini et al., Immunol. Today 8: 385–389 (1987)). This response has been particularly well studied for melanomas, and MLTC have been carried out either with peripheral blood cells or with tumor infiltrating lymphocytes. Examples of the literature in this area including Knuth et al., Proc. Natl. Acad. Sci. USA 86: 2804–2802 (1984); Mukherji et al., J. Exp. Med. 158: 240 (1983); Hérin et all, Int. J. Canc. 39: 390–396 (1987); Topalian et al, J. Clin. Oncol 6: 839–853 (1988). Stable cytolytic T cell clones ("CTLs" hereafter) have been derived from MLTC responder cells, and these clones are specific for the tumor cells. See Mukherji et al., supra, Hérin et all, supra, Knuth et al., supra. The antigens recognized on tumor cells by these autologous CTLs do not appear to represent a cultural artifact, since they are found on tumor cells in vivo. Topalian et al., supra; Degiovanni et al., Eur. J. Immunol. 20: 1865–1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid molecules which code for tumor rejection antigen precursors, including, but not being limited to those most characteristic of a particular tumor, with ramifications that are described infra.

Additional work has focused upon the presentation of TRAs by the class of molecules known as human leukocyte antigens, or "HLAs". This work has resulted in several unexpected discoveries regarding the field. Specifically in U.S. patent application Ser. No. 938,334, now abandoned, the disclosure of which is incorporated by reference, non-apeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446 now abandoned, filed Jan. 22, 1993 and incorporated by reference, the fact that the MAGE-1 expression product is processed to a second TRA is disclosed. This second TRA is presented by HLA-C-clone-10 molecules. The disclosure shows that a given TRAP can yield a plurality of TRAs.

In U.S. patent application Ser. No. 994,928 now abandoned, filed Dec. 22, 1992, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

The prior applications cited supra discussed antibodies against tumor rejection antigen precursors generally. The present investigators have utilized the isolated nucleic acid molecule coding for MAGE-1 to produce a recombinant MAGE-1 protein, and peptides derived therefrom. These have been used to produce polyclonal and monoclonal antibodies which specifically bind to MAGE-1. These antibodies, and their use, constitute the invention described and claimed herein.

BRIEF DESCRIPTION OF THE FIGURES

FIG. 2A shows silver stained SDS-polyacrylamide gels of affinity purified, MAGE-1 recombinant protein.

FIG. 2B presents immunoblotting work where recombinant MAGE-1 protein was used against rabbit antisera derived from immunization with three peptides (SEQ ID NOS: 2, 3 and 4). Blotting was at 1:1000 dilution. As a control, recombinant mouse p53 was used.

FIG. 3A shows the reactivity pattern of mAb MA 454 against six melanoma lines.

FIG. 3B shows the results obtained using rabbit polyclonal antisera against the same lines.

FIG. 3C shows results obtained with a MAGE-1 transfected cell line (MZ2-MEL 2.2-ET. 1), and its parent (MZ2-MEL 2.2).

DETAILED DESCRIPTION OF PREFERRED EMBODIMENTS

Many different "MAGE" genes have been identified, as will be seen from the applications and references cited supra. The MAGE-1 gene is at issue in the present case, and is the only one discussed hereafter. For convenience, it is presented herein as SEQ ID NO: 1.

"MAGE" as used herein refers to a nucleic acid sequence isolated from human cells.

When "TRAP" or "TRAs" are discussed herein as being specific to a tumor type, this means that the molecule under consideration is associated with that type of tumor, although not necessarily to the exclusion of other tumor types.

EXAMPLE 1

The cell line MZ2-MEL 3.1 described in, e.g., Van den Eynde et al., Int. J. Cancer 44: 634–640 (1989) and in the parent application cited supra, previously observed to express MAGE-1, was used as a source of total RNA. The total RNA was extracted from the cells, and was then subjected to reverse transcription/polymerase chain reaction, using the primers CHO8 and CHO9, as described by Van der Bruggen et al., Science 254: 1643–1647 (Dec. 13, 1991), the disclosure of which is incorporated by reference. This paper describes the "RT-PCR" technique, as does Brasseur et al., Int. J. Cancer 52: 839–841 (1992). It must be understood, however, that the sequence of MAGE-1 is known to the art, and other primers could be used besides CHO8 and CHO9.

Once the RT-PCR protocols were completed, the products were cloned directly into plasmid pT7 Blue (Novagen, Madison Wis.), following manufacturer's instructions which constituted well known techniques. Following the cloning, the recombinant plasmid DNA was treated with restriction endonucleases to generate fragments which included fragments containing the MAGE-1 gene. See, e.g. Van der Bruggen et al, supra.

The appropriate cDNA insert was subcloned unidirectionally, into plasmids pQE9, pQE10 and pQE11, using BamHI and HindIII cloning sites in pT7 Blue. The plasmids were transfected into E. coli, and recombinant protein production was induced via IPTG, as the host plasmid contains the lac operon. This yielded a fusion protein containing the MAGE-1 polypeptide sequence, which could be purified via $Ni^{2+}$ ion affinity chromatography.

Figure 1:
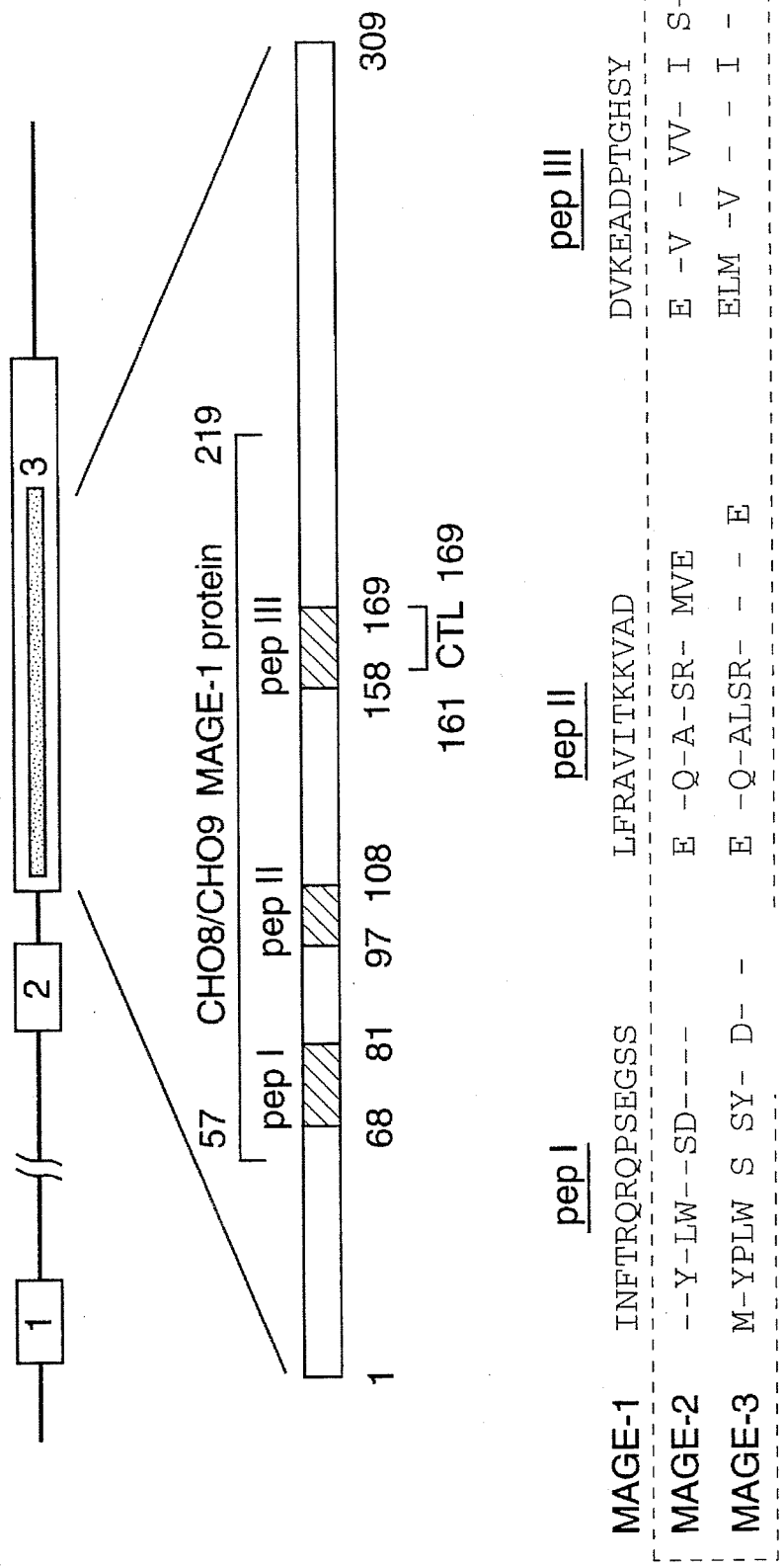
FIG. 1 shows, schematically, the MAGE-1 gene, oligopeptides derived from the recombinant MAGE-1 protein, and comparison with corresponding sequences in MAGE-2 and MAGE-3 deduced amino acid sequences.

The DNA sequence of the recombinant clone was obtained, and was confirmed to encode 163 amino acids which correspond to deduced amino acids 57–219 of the predicted MAGE-1 amino sequence, plus 30 residues from the plasmid itself. FIG. 1 shows this. The expected molecular mass is about 20–22 kDa.

When clones in pQE10 were studied, indeed, a recombinant protein of about 20 kDa was produced following IPTG induction. Other minor protein species of 70 kDa, 43 kDa, 17 kDa and 15 kDa were also found, as is seen in FIG. 2A.

EXAMPLE 2

The following describes procedures used to produce antibodies to MAGE-1. Based upon the predicted MAGE-1 amino acid sequence, three oligopeptides were prepared:

Ile Asn Phe Thr Arg Gln Arg Gln Pro Ser Glu Gly Ser Ser
(SEQ ID NO: 2)

Leu Phe Arg Ala Val Ile Thr Lys Lys Val Ala Asp
( SEQ ID NO: 3 )

Asp Val Lys Glu Ala Asp Pro Thr Gly His Ser Tyr
(SEQ ID NO: 4)

Rabbits were immunized with the peptides, and were then treated to collect antiserum.

Antisera prepared against these three peptides were then used with E. coli produced, recombinant MAGE-1 protein, in immunoblotting experiments. The results, set forth in FIG. 2B, show that only antiserum raised against the first of these peptides, i.e., SEQ ID NO: 2 reacted strongly. The fact that additional protein species that copurified with the 20 kDa fusion protein also showed reactivity, suggests that these are aggregates of the fusion protein. The peptide used corresponds to deduced amino acids 68–81 of the MAGE-1 of the predicted MAGE-1 protein.

When immunoblotting was carried out using lysates of melanoma cell line MZ2-MEL 3.1, no detectable MAGE protein was found.

EXAMPLE 3

Monoclonal antibodies were then prepared. Purified recombinant protein, produced as described supra, was used to immunize BALB/C mice. Hybridomas were generated and cloned. The protocol used was that described by Dippold et al., Proc. Natl. Acad. Sci. USA 77: 6114–6118 (1980), the disclosure of which is incorporated by reference. The key difference, of course, was the immunogen used for immunization.

Once hybridomas were generated, their supernatants were screened using a standard, solid phase ELISA on microtiter plates, using the immunizing fusion protein as target antigen. Five clones were found to be reactive. They all also showed moderate to strong reactivity in immunoblots.

As a control, mouse p53 protein, expressed in the same plasmid vector, was also tested. No reactivity was seen. These results are summarized in Table 1 which follows:

TABLE 1

Reactivity of mouse anti-recombinant MAGE-1 mAbs toward recombinant MAGE-1 protein and control p53 protein

| | Assay | | | |
|---|---|---|---|---|
| | ELISA | | Immunoblot | |
| mAb | MAGE-1 | p53 | MAGE-1 | p53 |
| MA32 | ++* | – | ++# | – |
| MA231 | + | – | ++ | – |
| MA399 | ++ | – | ++ | – |

TABLE 1-continued

Reactivity of mouse anti-recombinant MAGE-1 mAbs
toward recombinant MAGE-1 protein and control p53 protein

| | Assay | | | |
|---|---|---|---|---|
| | ELISA | | Immunoblot | |
| mAb | MAGE-1 | p53 | MAGE-1 | p53 |
| MA430 | ++ | − | +++ | − |
| MA454 | ++ | − | +++ | − |

*ELISA titer using hybridoma supernatants: −, <1:16; +, 1:64; ++, 1:256.
Immunoblot signal intensity: −, negative; +, weak; ++, moderate; +++, strong.

EXAMPLE 4

The mAbs described supra were then tested against lysates of melanoma cell lines. The cell lines tested, i.e., MZ2-MEL 3.1, MZ2-MEL 2.2, and SK-MEL-187, are all well known. MZ2-MEL 2.2 is a MAGE-1 loss variant derived from MAGE-1 positive parental MZ2-MEL 3.1 by CTL selection (van der Bruggen et al., Int. J. Cancer 44: 634–640 (1989)). These cells had been "typed" by RT-PCR as being MAGE-$1^+2^+3^+$ (MZ2-MEL 3.1), MAGE-$1^-2^+3^+$ (MZ2-MEL 2.2), and MAGE $1^-2^-3^-$ (SK MEL-187). The lysates were prepared by homogenizing the cells in Nonidet P40 (NP-40) buffer (1% NP-40, 50 mM Tris-HCl, pH 8.0, 150 mM NaCl). The results are shown in FIG. 3A.

Monoclonal antibody MA 454 reacted with a 46 kDa protein present in MZ2-MEL 3.1 lysate, but not in lysates of either of the other two cell lines. When three additional melanoma lines were tested, only those which were typed as being MAGE-1 positive reacted with the mAb. Expression of MAGE-2 or MAGE-3 was irrelevant.

The polyclonal antiserum in rabbits was also tested against these lysates. The immunogen was the fusion protein prepared in *E. coli*, described supra. Results are shown in FIG. 3B. It was positive for MZ2-MEL 3.1, and for MAGE-1 transfected cell line MZ2-MEL 2.2-ET.1, but was negative for parental line MZ2-MEL 2.2.

EXAMPLE 5

Lysates were prepared from liver, kidney and testis tissue, and from four melanoma cell lines including one MAGE-$1^+2^+3^+$ line, two MAGE-$1^-2^+3^+$, and one MAGE-$1^-2^-3^-$ lines. The lysates were prepared as described supra. When immunoblotting was carried out, testis lysates were positive with mAb 454, as were MAGE-1 positive melanomas. No other lysates were positive, which is in complete agreement with mRNA expression data.

Figure 4B:
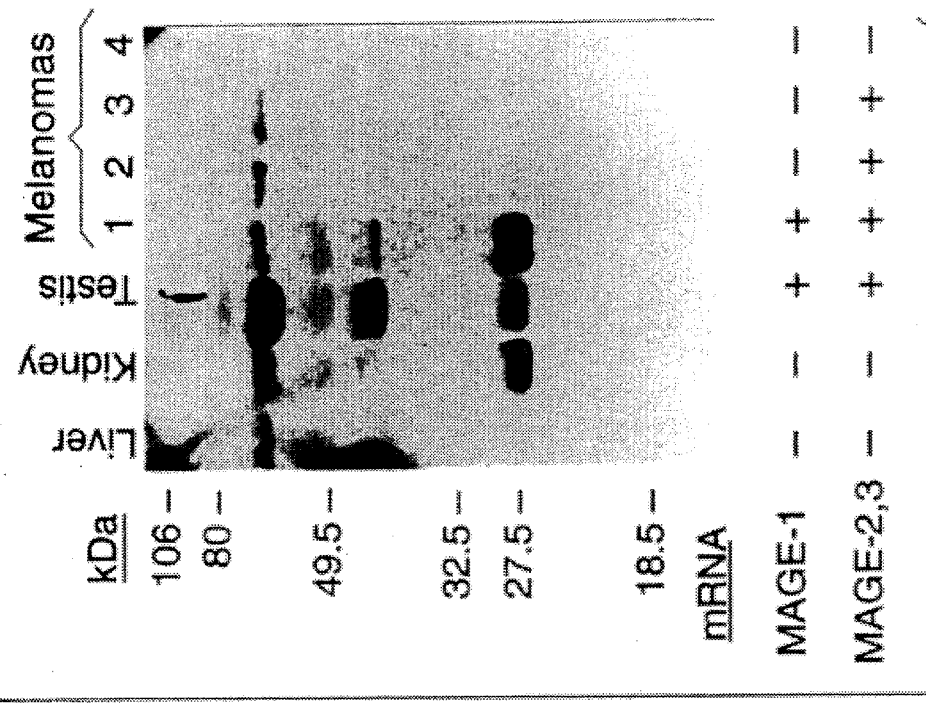
FIGS. 4A–C presents immunoblot analysis using the antibodies against tissue lysates.
Figure 4A:
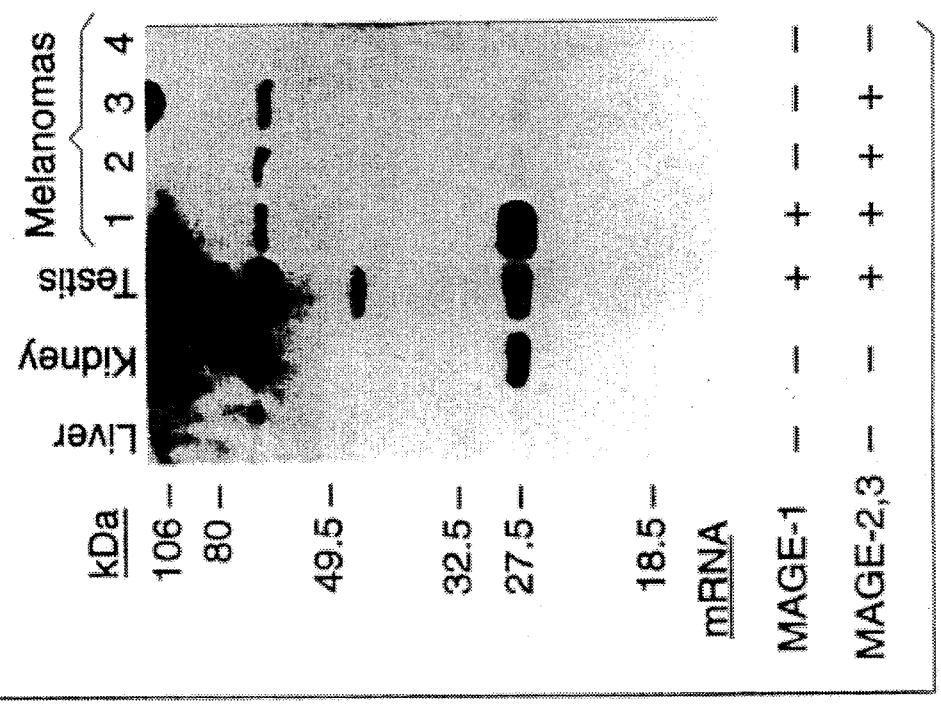
Figure 4C:
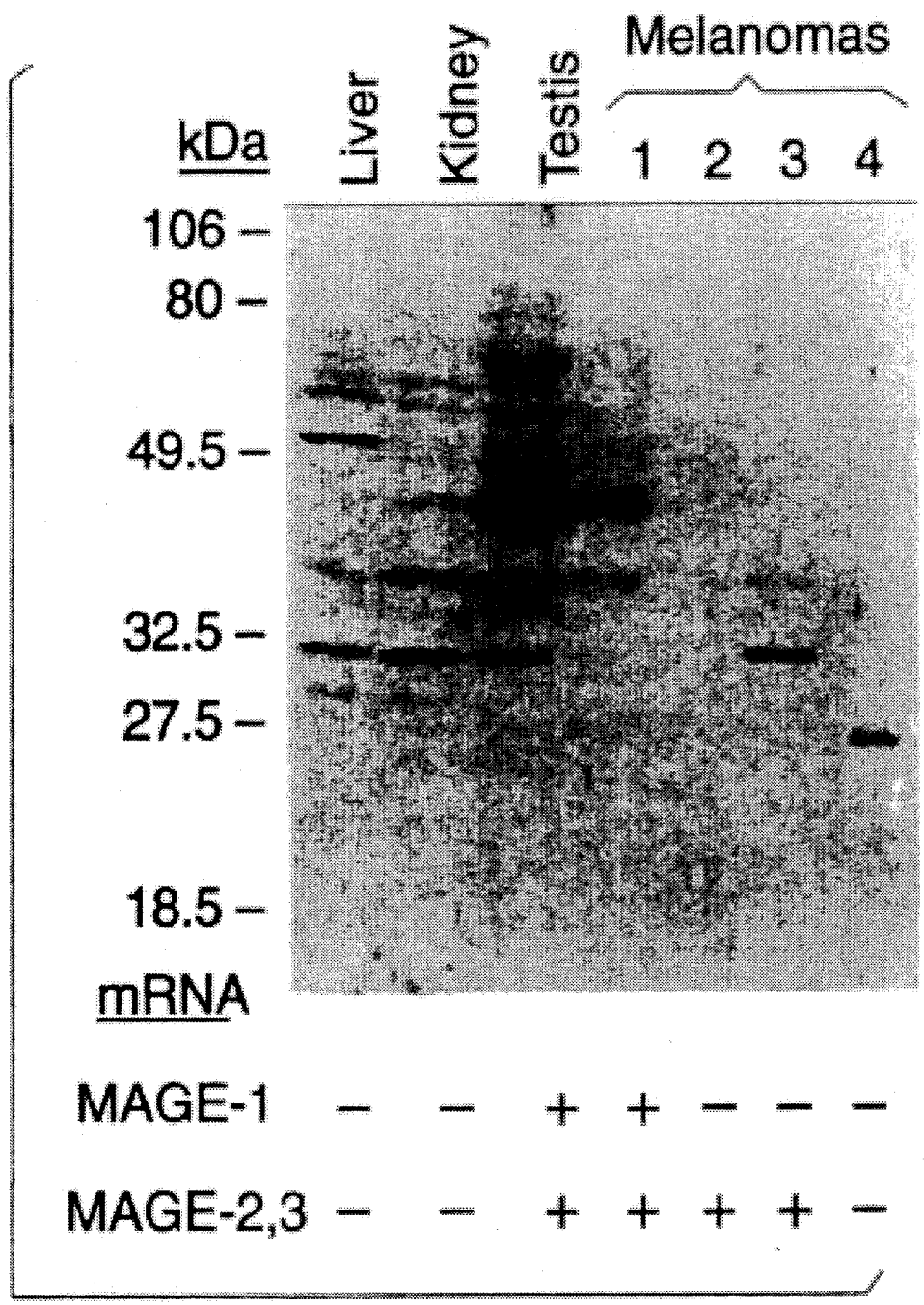

The same experiments were carried out using polyclonal antiserum, and the results paralleled those for the monoclonal antibodies. FIG. 4 presents these results.

The foregoing experiments describe the production of monoclonal antibodies which specifically bind to a tumor rejection antigen precursor TRAP. The studies show binding both to the "wild type" MAGE-1 molecule, and the recombinant form, but not to either of MAGE-2 or MAGE-3. A particularly preferred species of MAGE-1 binding mAb, i.e., MA454, has been deposited at the American Type Culture Collection 12301 Parklawn Drive, Rockville, Md. 20852, on Feb. 1, 1994 under Accession Number HB 11540.

The invention thus relates to MAGE-1 specific monoclonal antibodies and the hybridomas which produce them. The mAbs were found to be useful in determining expression of MAGE-1 in cell lysates. Specifically, the mAbs can be added, e.g., in labelled form, bound to a solid phase, or otherwise treated to increase the sensitivity of MAGE-1 detection. Any of the standard types of immunoassays, including ELISAs, RIAs, competitive assays, agglutination assays, and all others are encompassed with respect to the way the mAbs can be used. "Cell lysate" as used herein refers not only to a sample which is expressly lysed, but also to those samples which contain cells which have been lysed in vivo, or any sample which contains material normally internal to the cells. The detection of MAGE-1 expression product is useful, e.g., in diagnosing or monitoring the presence or progress of a cancer.

The isolated, recombinant MAGE-1 protein is also a feature of this invention. This molecule has a molecular weight of about 20–22 kDa as determined by SDS-PAGE, and is useful as an immunogen as are the peptides of SEQ ID NOS: 2, 3 and 4, shown by the examples to be immunogenic. Preferably, these are used in combination with a suitable adjuvant. The isolated form of the molecule obtained via non-recombinant means has a molecular weight of about 43 kd as determined by SDS-PAGE, and is useful in the same ways as is the recombinant protein. The recombinant form may consist of only amino acids 57–219 of the sequence of MAGE-1, as shown supra. Also a part of the invention is the full length isolated, recombinant MAGE-1 protein, having a molecular weight of about 34.3 kd as determined by SDS-PAGE, and consisting of the amino acid sequence coded for by nucleotides 3931–4761 of SEQ ID NO: 1.

Other features of the invention will be clear to the artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Monoclonal antibody which specifically binds to tumor rejection antigen precursor MAGE-1.

2. The monoclonal antibody of claim 1, designated MA454 produced by the hybridoma having A.T.C.C. Accession Number HB 11540.

3. Hybridoma cell line which produces the monoclonal antibody of claim 1.

4. The hybridoma cell line of claim 3, designated A.T.C.C. Accession No. HB 11540 and wherein said monoclonal antibody is MA454.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
      ( A ) LENGTH: 5674 base pairs ( B ) TYPE: nucleic acid
( C ) STRANDEDNESS: single
( D ) TOPOLOGY: linear ( i i ) MOLECULE TYPE: genomic DNA ( i x ) FEATURE:
( A ) NAME/KEY: MAGE-1 gene ( x i ) SEQUENCE DESCRIPTION: SEQ ID NO: 1:

| | | | | | |
|---|---|---|---|---|---|
| CCCGGGGCAC | CACTGGCATC | CCTCCCCCTA | CCACCCCCAA | TCCCTCCCTT | 50 |
| TACGCCACCC | ATCCAAACAT | CTTCACGCTC | ACCCCCAGCC | CAAGCCAGGC | 100 |
| AGAATCCGGT | TCCACCCCTG | CTCTCAACCC | AGGGAAGCCC | AGGTGCCCAG | 150 |
| ATGTGACGCC | ACTGACTTGA | GCATTAGTGG | TTAGAGAGAA | GCGAGGTTTT | 200 |
| CGGTCTGAGG | GGCGGCTTGA | GATCGGTGGA | GGGAAGCGGG | CCCAGCTCTG | 250 |
| TAAGGAGGCA | AGGTGACATG | CTGAGGGAGG | ACTGAGGACC | CACTTACCCC | 300 |
| AGATAGAGGA | CCCCAAATAA | TCCCTTCATG | CCAGTCCTGG | ACCATCTGGT | 350 |
| GGTGGACTTC | TCAGGCTGGG | CCACCCCCAG | CCCCCTTGCT | GCTTAAACCA | 400 |
| CTGGGGACTC | GAAGTCAGAG | CTCCGTGTGA | TCAGGAAGG | GCTGCTTAGG | 450 |
| AGAGGGCAGC | GTCCAGGCTC | TGCCAGACAT | CATGCTCAGG | ATTCTCAAGG | 500 |
| AGGGCTGAGG | GTCCCTAAGA | CCCCACTCCC | GTGACCCAAC | CCCCACTCCA | 550 |
| ATGCTCACTC | CCGTGACCCA | ACCCCTCTT | CATTGTCATT | CCAACCCCCA | 600 |
| CCCCACATCC | CCCACCCCAT | CCCTCAACCC | TGATGCCCAT | CCGCCCAGCC | 650 |
| ATTCCACCCT | CACCCCCACC | CCCACCCCCA | CGCCCACTCC | CACCCCCACC | 700 |
| CAGGCAGGAT | CCGGTTCCCG | CCAGGAAACA | TCCGGGTGCC | CGGATGTGAC | 750 |
| GCCACTGACT | TGCGCATTGT | GGGGCAGAGA | GAAGCGAGGT | TTCCATTCTG | 800 |
| AGGGACGGCG | TAGAGTTCGG | CCGAAGGAAC | CTGACCCAGG | CTCTGTGAGG | 850 |
| AGGCAAGGTG | AGAGGCTGAG | GGAGGACTGA | GGACCCCGCC | ACTCCAAATA | 900 |
| GAGAGCCCCA | AATATTCCAG | CCCCGCCCTT | GCTGCCAGCC | CTGGCCCACC | 950 |
| CGCGGGAAGA | CGTCTCAGCC | TGGGCTGCCC | CCAGACCCCT | GCTCCAAAAG | 1000 |
| CCTTGAGAGA | CACCAGGTTC | TTCTCCCCAA | GCTCTGGAAT | CAGAGGTTGC | 1050 |
| TGTGACCAGG | GCAGGACTGG | TTAGGAGAGG | GCAGGGCACA | GGCTCTGCCA | 1100 |
| GGCATCAAGA | TCAGCACCCA | AGAGGGAGGG | CTGTGGGCCC | CAAGACTGC | 1150 |
| ACTCCAATCC | CCACTCCCAC | CCCATTCGCA | TTCCCATTCC | CCACCCAACC | 1200 |
| CCCATCTCCT | CAGCTACACC | TCCACCCCCA | TCCCTACTCC | TACTCCGTCA | 1250 |
| CCTGACCACC | ACCCTCCAGC | CCCAGCACCA | GCCCAACCC | TTCTGCCACC | 1300 |
| TCACCCTCAC | TGCCCCCAAC | CCCACCCTCA | TCTCTCTCAT | GTGCCCCACT | 1350 |
| CCCATCGCCT | CCCCCATTCT | GGCAGAATCC | GGTTTGCCCC | TGCTCTCAAC | 1400 |
| CCAGGGAAGC | CCTGGTAGGC | CCGATGTGAA | ACCACTGACT | TGAACCTCAC | 1450 |
| AGATCTGAGA | GAAGCCAGGT | TCATTTAATG | GTTCTGAGGG | GCGGCTTGAG | 1500 |
| ATCCACTGAG | GGGAGTGGTT | TTAGGCTCTG | TGAGGAGGCA | AGGTGAGATG | 1550 |
| CTGAGGGAGG | ACTGAGGAGG | CACACACCCC | AGGTAGATGG | CCCCAAAATG | 1600 |
| ATCCAGTACC | ACCCCTGCTG | CCAGCCCTGG | ACCACCGGC | CAGGACAGAT | 1650 |
| GTCTCAGCTG | GACCACCCCC | CGTCCCGTCC | CACTGCCACT | TAACCCACAG | 1700 |
| GGCAATCTGT | AGTCATAGCT | TATGTGACCG | GGGCAGGGTT | GGTCAGGAGA | 1750 |

| | | | | |
|---|---|---|---|---|
| GGCAGGGCCC | AGGCATCAAG | GTCCAGCATC | CGCCCGGCAT | TAGGGTCAGG | 1800 |
| ACCCTGGGAG | GGAACTGAGG | GTTCCCCACC | CACACCTGTC | TCCTCATCTC | 1850 |
| CACCGCCACC | CCACTCACAT | TCCCATACCT | ACCCCTACC | CCCAACCTCA | 1900 |
| TCTTGTCAGA | ATCCCTGCTG | TCAACCCACG | GAAGCACGG | GAATGGCGGC | 1950 |
| CAGGCACTCG | GATCTTGACG | TCCCCATCCA | GGGTCTGATG | GAGGGAAGGG | 2000 |
| GCTTGAACAG | GGCCTCAGGG | GAGCAGAGGG | AGGGCCCTAC | TGCGAGATGA | 2050 |
| GGGAGGCCTC | AGAGGACCCA | GCACCCTAGG | ACACCGCACC | CCTGTCTGAG | 2100 |
| ACTGAGGCTG | CCACTTCTGG | CCTCAAGAAT | CAGAACGATG | GGGACTCAGA | 2150 |
| TTGCATGGGG | GTGGGACCCA | GGCCTGCAAG | GCTTACGCGG | AGGAAGAGGA | 2200 |
| GGGAGGACTC | AGGGGACCTT | GGAATCCAGA | TCAGTGTGGA | CCTCGGCCCT | 2250 |
| GAGAGGTCCA | GGGCACGGTG | GCCACATATG | GCCCATATTT | CCTGCATCTT | 2300 |
| TGAGGTGACA | GGACAGAGCT | GTGGTCTGAG | AAGTGGGGCC | TCAGGTCAAC | 2350 |
| AGAGGGAGGA | GTTCCAGGAT | CCATATGGCC | CAAGATGTGC | CCCCTTCATG | 2400 |
| AGGACTGGGG | ATATCCCCGG | CTCAGAAAGA | AGGGACTCCA | CACAGTCTGG | 2450 |
| CTGTCCCCTT | TTAGTAGCTC | TAGGGGGACC | AGATCAGGGA | TGGCGGTATG | 2500 |
| TTCCATTCTC | ACTTGTACCA | CAGGCAGGAA | GTTGGGGGGC | CCTCAGGGAG | 2550 |
| ATGGGGTCTT | GGGGTAAAGG | GGGGATGTCT | ACTCATGTCA | GGGAATTGGG | 2600 |
| GGTTGAGGAA | GCACAGGCGC | TGGCAGGAAT | AAAGATGAGT | GAGACAGACA | 2650 |
| AGGCTATTGG | AATCCACACC | CCAGAACCAA | AGGGGTCAGC | CCTGGACACC | 2700 |
| TCACCCAGGA | TGTGGCTTCT | TTTTCACTCC | TGTTTCCAGA | TCTGGGGCAG | 2750 |
| GTGAGGACCT | CATTCTCAGA | GGGTGACTCA | GGTCAACGTA | GGGACCCCCA | 2800 |
| TCTGGTCTAA | AGACAGAGCG | GTCCCAGGAT | CTGCCATGCG | TTCGGGTGAG | 2850 |
| GAACATGAGG | GAGGACTGAG | GGTACCCCAG | GACCAGAACA | CTGAGGGAGA | 2900 |
| CTGCACAGAA | ATCAGCCCTG | CCCCTGCTGT | CACCCAGAG | AGCATGGGCT | 2950 |
| GGGCCGTCTG | CCGAGGTCCT | TCCGTTATCC | TGGGATCATT | GATGTCAGGG | 3000 |
| ACGGGGAGGC | CTTGGTCTGA | GAAGGCTGCG | CTCAGGTCAG | TAGAGGGAGC | 3050 |
| GTCCAGGCC | CTGCCAGGAG | TCAAGGTGAG | GACCAAGCGG | GCACCTCACC | 3100 |
| CAGGACACAT | TAATTCCAAT | GAATTTTGAT | ATCTCTTGCT | GCCCTTCCCC | 3150 |
| AAGGACCTAG | GCACGTGTGG | CCAGATGTTT | GTCCCCTCCT | GTCCTTCCAT | 3200 |
| TCCTTATCAT | GGATGTGAAC | TCTTGATTTG | GATTTCTCAG | ACCAGCAAAA | 3250 |
| GGGCAGGATC | CAGGCCCTGC | CAGGAAAAAT | ATAAGGGCCC | TGCGTGAGAA | 3300 |
| CAGAGGGGT | CATCCACTGC | ATGAGAGTGG | GGATGTCACA | GAGTCCAGCC | 3350 |
| CACCCTCCTG | GTAGCACTGA | GAAGCCAGGG | CTGTGCTTGC | GGTCTGCACC | 3400 |
| CTGAGGGCCC | GTGGATTCCT | CTTCCTGGAG | CTCCAGGAAC | CAGGCAGTGA | 3450 |
| GGCCTTGGTC | TGAGACAGTA | TCCTCAGGTC | ACAGAGCAGA | GGATGCACAG | 3500 |
| GGTGTGCCAG | CAGTGAATGT | TTGCCCTGAA | TGCACACCAA | GGGCCCCACC | 3550 |
| TGCCACAGGA | CACATAGGAC | TCCACAGAGT | CTGGCCTCAC | CTCCCTACTG | 3600 |
| TCAGTCCTGT | AGAATCGACC | TCTGCTGGCC | GGCTGTACCC | TGAGTACCCT | 3650 |
| CTCACTTCCT | CCTTCAGGTT | TTCAGGGGAC | AGGCCAACCC | AGAGGACAGG | 3700 |
| ATTCCCTGGA | GGCCACAGAG | GAGCACCAAG | GAGAAGATCT | GTAAGTAGGC | 3750 |

```
CTTTGTTAGA GTCTCCAAGG TTCAGTTCTC AGCTGAGGCC TCTCACACAC       3800
TCCCTCTCTC CCCAGGCCTG TGGGTCTTCA TTGCCCAGCT CCTGCCCACA       3850
CTCCTGCCTG CTGCCCTGAC GAGAGTCATC                             3880
ATG TCT CTT GAG CAG AGG AGT CTG CAC TGC AAG CCT GAG GAA      3922
GCC CTT GAG GCC CAA CAA GAG GCC CTG GGC CTG GTG TGT GTG      3964
CAG GCT GCC ACC TCC TCC TCC TCT CCT CTG GTC CTG GGC ACC      4006
CTG GAG GAG GTG CCC ACT GCT GGG TCA ACA GAT CCT CCC CAG      4048
AGT CCT CAG GGA GCC TCC GCC TTT CCC ACT ACC ATC AAC TTC      4090
ACT CGA CAG AGG CAA CCC AGT GAG GGT TCC AGC AGC CGT GAA      4132
GAG GAG GGG CCA AGC ACC TCT TGT ATC CTG GAG TCC TTG TTC      4174
CGA GCA GTA ATC ACT AAG AAG GTG GCT GAT TTG GTT GGT TTT      4216
CTG CTC CTC AAA TAT CGA GCC AGG GAG CCA GTC ACA AAG GCA      4258
GAA ATG CTG GAG AGT GTC ATC AAA AAT TAC AAG CAC TGT TTT      4300
CCT GAG ATC TTC GGC AAA GCC TCT GAG TCC TTG CAG CTG GTC      4342
TTT GGC ATT GAC GTG AAG GAA GCA GAC CCC ACC GGC CAC TCC      4384
TAT GTC CTT GTC ACC TGC CTA GGT CTC TCC TAT GAT GGC CTG      4426
CTG GGT GAT AAT CAG ATC ATG CCC AAG ACA GGC TTC CTG ATA      4468
ATT GTC CTG GTC ATG ATT GCA ATG GAG GGC GGC CAT GCT CCT      4510
GAG GAG GAA ATC TGG GAG GAG CTG AGT GTG ATG GAG GTG TAT      4552
GAT GGG AGG GAG CAC AGT GCC TAT GGG GAG CCC AGG AAG CTG      4594
CTC ACC CAA GAT TTG GTG CAG GAA AAG TAC CTG GAG TAC GGC      4636
AGG TGC CGG ACA GTG ATC CCG CAC GCT ATG AGT TCC TGT GGG      4678
GTC CAA GGG CCC TCG CTG AAA CCA GCT ATG TGA                  4711
AAGTCCTTGA GTATGTGATC AAGGTCAGTG CAAGAGTTC                   4750
GCTTTTCTT CCCATCCCTG CGTGAAGCAG CTTTGAGAGA GGAGGAAGAG        4800
GGAGTCTGAG CATGAGTTGC AGCCAAGGCC AGTGGGAGGG GGACTGGGCC       4850
AGTGCACCTT CCAGGGCCGC GTCCAGCAGC TTCCCCTGCC TCGTGTGACA       4900
TGAGGCCCAT TCTTCACTCT GAAGAGAGCG GTCAGTGTTC TCAGTAGTAG       4950
GTTTCTGTTC TATTGGGTGA CTTGGAGATT TATCTTTGTT CTCTTTTGGA       5000
ATTGTTCAAA TGTTTTTTTT TAAGGGATGG TTGAATGAAC TTCAGCATCC       5050
AAGTTTATGA ATGACAGCAG TCACACAGTT CTGTGTATAT AGTTTAAGGG       5100
TAAGAGTCTT GTGTTTTATT CAGATTGGGA AATCCATTCT ATTTGTGAA        5150
TTGGGATAAT AACAGCAGTG GAATAAGTAC TTAGAAATGT GAAAAATGAG       5200
CAGTAAAATA GATGAGATAA AGAACTAAAG AAATTAAGAG ATAGTCAATT       5250
CTTGCCTTAT ACCTCAGTCT ATTCTGTAAA ATTTTTAAAG ATATATGCAT       5300
ACCTGGATTT CCTTGGCTTC TTTGAGAATG TAAGAGAAAT TAAATCTGAA       5350
TAAAGAATTC TTCCTGTTCA CTGGCTCTTT TCTTCTCCAT GCACTGAGCA       5400
TCTGCTTTTT GGAAGGCCCT GGGTTAGTAG TGGAGATGCT AAGGTAAGCC       5450
AGACTCATAC CCACCCATAG GGTCGTAGAG TCTAGGAGCT GCAGTCACGT       5500
AATCGAGGTG GCAAGATGTC CTCTAAAGAT GTAGGGAAAA GTGAGAGAGG       5550
```

```
GGTGAGGGTG  TGGGGCTCCG  GGTGAGAGTG  GTGGAGTGTC  AATGCCCTGA        5600

GCTGGGGCAT  TTTGGGCTTT  GGGAAACTGC  AGTTCCTTCT  GGGGGAGCTG        5650

ATTGTAATGA  TCTTGGGTGG  ATCC                                      5674
```

( 2 ) INFORMATION FOR SEQ ID NO: 2:

( i ) SEQUENCE CHARACTERISTICS:
        ( A ) LENGTH: 14 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 2:

Ile  Asn  Phe  Thr  Arg  Gln  Arg  Gln  Pro  Ser  Glu  Gly  Ser  Ser
              5                              10

( 2 ) INFORMATION FOR SEQ ID NO: 3:

( i ) SEQUENCE CHARACTERISTICS:
        ( A ) LENGTH: 12 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 3:

Leu  Phe  Arg  Ala  Val  Ile  Thr  Lys  Lys  Val  Ala  Asp
              5                        10

( 2 ) INFORMATION FOR SEQ ID NO: 4:

( i ) SEQUENCE CHARACTERISTICS:
        ( A ) LENGTH: 12 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 4:

Asp  Val  Lys  Glu  Ala  Asp  Pro  Thr  Gly  His  Ser  Tyr
              5                        10